(12) United States Patent
Mompon

US010178872B2

(10) Patent No.: US 10,178,872 B2
(45) Date of Patent: Jan. 15, 2019

(54) METHOD FOR PRODUCING ARTICLES OF PLANT ORIGIN IMPREGNATED WITH A LIQUID PLANT SUBSTANCE

(75) Inventor: Bernard Mompon, Vannes (FR)

(73) Assignee: Schweitzer-Manduit International, Inc., Alpharetta, GA (US)

( * ) Notice: Subject to any disclaimer, the term of this patent is extended or adjusted under 35 U.S.C. 154(b) by 875 days.

(21) Appl. No.: 13/882,391

(22) PCT Filed: Oct. 13, 2011

(86) PCT No.: PCT/FR2011/052393
§ 371 (c)(1),
(2), (4) Date: Jul. 9, 2013

(87) PCT Pub. No.: WO2012/056141
PCT Pub. Date: May 3, 2012

(65) Prior Publication Data
US 2013/0280320 A1    Oct. 24, 2013

(30) Foreign Application Priority Data
Oct. 29, 2010 (FR) ..................... 10 58969

(51) Int. Cl.
| | | |
|---|---|---|
| A61K 36/00 | (2006.01) |
| A61K 36/16 | (2006.01) |
| A61K 36/258 | (2006.01) |
| A61K 36/38 | (2006.01) |
| A61K 36/48 | (2006.01) |
| A61K 36/76 | (2006.01) |
| A61K 36/282 | (2006.01) |
| A61K 36/70 | (2006.01) |
| A23L 1/00 | (2006.01) |
| A23F 3/14 | (2006.01) |
| A23F 3/40 | (2006.01) |
| A61K 8/02 | (2006.01) |
| A61K 8/97 | (2017.01) |
| A61Q 19/00 | (2006.01) |
| C11B 9/02 | (2006.01) |
| A61K 9/70 | (2006.01) |
| A61K 36/53 | (2006.01) |
| A61K 36/534 | (2006.01) |
| C12P 19/14 | (2006.01) |

(Continued)

(52) U.S. Cl.
CPC .............. *A23L 1/0073* (2013.01); *A23F 3/14* (2013.01); *A23F 3/405* (2013.01); *A23L 27/10* (2016.08); *A23L 27/36* (2016.08); *A23L 27/70* (2016.08); *A23L 33/105* (2016.08); *A23P 30/10* (2016.08); *A61K 8/0208* (2013.01); *A61K 8/97* (2013.01); *A61K 9/7007* (2013.01); *A61K 36/00* (2013.01); *A61K 36/53* (2013.01); *A61K 36/534* (2013.01); *A61Q 19/00* (2013.01); *C11B 9/02* (2013.01); *C11B 9/025* (2013.01); *C11B 9/027* (2013.01); *C12P 19/14* (2013.01)

(58) Field of Classification Search
CPC ...... A61K 36/16; A61K 36/25; A61K 36/282; A61K 36/38; A61K 36/9066
USPC ....... 424/725, 729, 730, 757, 756, 740, 775, 424/774
See application file for complete search history.

(56) References Cited

U.S. PATENT DOCUMENTS 3,353,541 A    11/1967 Hind et al.
3,386,449 A    6/1968 Hind
(Continued)

FOREIGN PATENT DOCUMENTS

CN    1329855 A    1/2002
CN    1565286 A    1/2005
(Continued)

OTHER PUBLICATIONS

Raventos et al (Food Science Tech. Int. (2002), vol. 8 (5), pp. 269-284).*

(Continued)

*Primary Examiner* — Christopher R Tate
*Assistant Examiner* — Deborah A Davis
(74) *Attorney, Agent, or Firm* — Dority & Manning, P.A.

(57) ABSTRACT

The present invention relates to a method for producing articles impregnated with at least one plant substance from at least one plant, characterized in that it comprises the following steps:
a) Extraction and/or pressing of at least one plant (V1), or at least one part of said plant, producing a liquid plant extract (E1)) and a solid fibrous residue (R1), then
b) Separation of said plant extract (E1) from said fibrous residue (R1), and
c) Destructuring of said fibrous residue (R1),
d) Production of a fibrous web or of an article made from the fibrous residue (R1) obtained in step c), and
e) Impregnation of said fibrous residue (R1) with (i) at least said plant extract (E1), which is optionally concentrated, purified, flavored and/or fragranced, with (ii) at least one water-soluble or liposoluble plant substance isolated from said plant extract (E1), with (iii) at least one composition comprising at least one optionally concentrated, purified, flavored and/or fragranced water-soluble or liposoluble substance of said plant extract (E1), or with (iv) at least one plant extract (E2) or at least one composition comprising at least one optionally concentrated, purified, flavored and/or fragranced water-soluble or liposoluble substance of said plant extract (E2), resulting from an extraction or pressing of a plant (V2) different from said plant (V1).

18 Claims, 3 Drawing Sheets

(51) Int. Cl.
*A23P 30/10* (2016.01)
*A23L 27/00* (2016.01)
*A23L 27/10* (2016.01)
*A23L 27/30* (2016.01)
*A23L 33/105* (2016.01)

(56) References Cited

U.S. PATENT DOCUMENTS

| | | |
|---|---|---|
| 3,415,253 A | 12/1968 | Michels et al. |
| 3,420,241 A | 1/1969 | Hind et al. |
| 3,428,053 A | 2/1969 | Schoenbaum et al. |
| 3,467,109 A | 9/1969 | Block et al. |
| 3,483,874 A | 12/1969 | Hind |
| 3,561,451 A | 2/1971 | Jacin et al. |
| 3,760,815 A | 9/1973 | Deszyck |
| 3,847,164 A | 11/1974 | Mattina et al. |
| 3,860,012 A | 1/1975 | Selke |
| 4,182,349 A | 1/1980 | Selke |
| 4,674,519 A | 6/1987 | Keritsis et al. |
| 4,891,232 A | 1/1990 | Dahl |
| 5,099,862 A * | 3/1992 | White .......... A24B 15/24 131/297 |
| 5,529,796 A | 6/1996 | Gobbo |
| 5,715,844 A | 2/1998 | Young et al. |
| 5,724,998 A | 3/1998 | Gellatly et al. |
| 5,765,570 A | 6/1998 | Litzinger et al. |
| 6,761,918 B2 | 7/2004 | Pulikkottil et al. |
| 6,818,234 B1 | 11/2004 | Nair et al. |
| 7,001,629 B1 | 2/2006 | Mengal et al. |
| 7,793,585 B2 | 9/2010 | Ramussen |
| 8,499,965 B2 | 8/2013 | Sheffield |
| 8,597,667 B2 | 12/2013 | Mou et al. |
| 8,734,881 B2 | 5/2014 | Yoakim et al. |
| 9,220,296 B2 | 12/2015 | Fall et al. |
| 2002/0132098 A1 | 9/2002 | Miyazawa et al. |
| 2003/0004479 A1 | 1/2003 | Ueda et al. |
| 2003/0113411 A1 | 6/2003 | Rose |
| 2003/0187055 A1 | 10/2003 | Riker |
| 2004/0156920 A1 | 8/2004 | Kane |
| 2004/0180077 A1 | 9/2004 | Riker |
| 2005/0064049 A1 | 3/2005 | Mori et al. |
| 2005/0088632 A1 | 4/2005 | Sadi |
| 2005/0158252 A1 | 7/2005 | Romanowski |
| 2006/0165756 A1 | 7/2006 | Catani |
| 2007/0199453 A1 | 8/2007 | Rasmussen |
| 2007/0243273 A1* | 10/2007 | Dev .......... A61K 31/12 424/751 |
| 2009/0047328 A1 | 2/2009 | Cunningham |
| 2009/0169654 A1 | 7/2009 | Banerjee |
| 2010/0032444 A1 | 2/2010 | Sheffield |
| 2010/0196545 A1 | 8/2010 | Buffet et al. |
| 2010/0210866 A1 | 8/2010 | Toyohara et al. |
| 2010/0233322 A1 | 9/2010 | Fukuda |
| 2011/0020512 A1 | 1/2011 | Masutake |
| 2011/0236502 A1 | 9/2011 | Guillory |
| 2013/0280320 A1 | 10/2013 | Mompon |
| 2014/0224265 A1 | 8/2014 | Rouillard et al. |
| 2014/0295049 A1 | 10/2014 | Ragot et al. |
| 2015/0037389 A1 | 2/2015 | Ragot et al. |
| 2015/0050371 A1 | 2/2015 | Gehling et al. |
| 2015/0056255 A1 | 2/2015 | Ragot et al. |
| 2015/0175810 A1 | 6/2015 | Rieland |
| 2015/0374624 A1 | 12/2015 | Ragot et al. |
| 2016/0255854 A1 | 9/2016 | Rousseau |

FOREIGN PATENT DOCUMENTS

| | | | |
|---|---|---|---|
| CN | 1957777 A | 5/2007 | |
| CN | 102919430 | 2/2012 | |
| CN | 103054156 | 4/2013 | |
| DE | 202010001912 U1 | 3/2011 | |
| GB | 1341069 | 12/1973 | |
| JP | H 09163930 A | 6/1997 | |
| JP | H10304822 | 11/1998 | |
| JP | 2001131866 A | 5/2001 | |
| JP | 2007098152 | 4/2004 | |
| JP | 2005119967 | 5/2005 | |
| JP | 2005119967 A * | 5/2005 | |
| JP | 2005306742 A | 11/2005 | |
| JP | 2006050934 A | 2/2006 | |
| JP | 2006246817 A | 9/2006 | |
| JP | 2006249599 A | 9/2006 | |
| JP | 2006256968 A | 9/2006 | |
| JP | 2008274535 A | 11/2008 | |
| JP | 2011182783 A | 9/2011 | |
| KR | 20070090286 | 9/2007 | |
| KR | 20100114348 | 10/2010 | |
| WO | WO-9409653 A1 * | 5/1994 | .......... A24B 15/282 |
| WO | WO 0205655 | 1/2002 | |

OTHER PUBLICATIONS

PCT/FR2011/052393 International Search Report and Written Opinion—Translation—dated May 25, 2013.
Co-pending U.S. Appl. No. 14/193,910 dated Feb. 28, 2014.
Blumenthal and al. Herbal Medicine, Expanded Commission E. Monographs, pp. 393-400.
Adams et al., Analysis of the Interactions of Botanical Extract Combinations Against the Viability of Prostate Cancer Cell Lines, Mar. 2003, pp. 117-124.
Lin et al., Inhibition of Helicobacter Pylori and Associated Urease by Oregano and Cranberry Phytochemical Synergies, Applied and Environmental Microbiology, Dec. 2005, vol. 71., No. 12, pp. 8558-8564.
Greer, C.C,. A Text-Book of Cooking; J.S. Cushing Co.—Berwick & Smith Co. Norwood, MA 1915, pp. 175-177.
Innovation Food Online, Sodium Alginate; URL<https://innovationinfood.wikispaces.com/Sodium+alginate> Published Jan. 4, 2007 Online, 7 pages with one extra page having google search hit with datestamp.
CN20090097787; Huimin, Y., dated Apr. 2009, English Abstract Only, 2 pages.
SU1161061; Choladze, et al., dated Jun. 1985, English Abstract Only, 2 pages.
Co-pending U.S. Appl. No. 15/053,134, dated Feb. 25, 2016.
Co-pending U.S. Appl. No. 15/506,620, filed Feb. 24, 2017.

* cited by examiner

METHOD FOR PRODUCING ARTICLES OF PLANT ORIGIN IMPREGNATED WITH A LIQUID PLANT SUBSTANCE

RELATED APPLICATIONS

The present application claims priority to PCT International Application Serial No. PCT/FR2011/052393 filed Oct. 13, 2011 and which claims filing benefit of FR Patent Application Serial No. 1058969 filed on Oct. 29, 2010, which are both hereby incorporated by reference in their entirety.

TECHNICAL FIELD

The present invention relates to a method for producing articles of plant origin impregnated with at least one liquid vegetal substance, advantageously of the same plant origin. Advantageously, the vegetal substance is a plant. The invention also relates to the articles thus produced, which may have multiple applications, in particular in the agri-food sector, phytotherapy, cosmetics, pharmacy, herbal uses, nutraceutical products and herbal tea-making.

BACKGROUND OF THE INVENTION

The traditional scientific classifications group together, under the term "plant," several lines of living organisms which, according to the etymological origin of the term, vegetate.

Plants consist of cells organized in leaves, stems, roots, flowers and seeds. Plant cells are characterized by a plant cell wall made from cellulose. All plant cells have a thin and flexible primary membrane which, when the cells come together, form a much thicker and rigid so-called secondary wall. The cells are then glued to each other by a pectin-rich middle gill. While the primary wall is made up of cellulose, hemicellulose, pectin, various proteins, and polysaccharides acting as binders between the various cellulose fibers, the secondary wall is much thicker and richer in cellulose than the primary membrane. It contains lignin, which is a hydrophobic polyphenolic polymer that makes the secondary wall rigid and relatively impermeable to water and solvents.

Whole plants or plant parts are sources of various ingredients and biologically active molecules that are widely used to nourish, treat, perfume, and improve the hygiene and beauty of human beings. These substances of interest may be extracted from plants and plant parts using various physical methods.

However, the industrial and personal extraction (during the preparation of a cup of tea or herbal tea, for example) is not always easy. In fact, it is generally incomplete, in particular due to walls, bark, ribs and fibers of the plants, but in particular because the walls of the plant cells, and in particular the lignin and cellulose fibers, oppose the extraction of the substances of interest located in the plant cells, in particular in the various vacuoles and organelles, such as nuclei, mitochondria, chloroplasts, endoplasmic reticula, ribosomes and Golgi bodies, among others.

That is why a certain number of more or less brutal treatments must generally be applied to the plants or plant parts before their extraction so as to break down the physical barrier made up of the walls of the plant cells. Methods making it possible to eliminate the aforementioned obstacles in particular include: threshing, drying, desiccation, grinding, freezing, cryogrinding, pelletizing (extrusion), enzyme treatment (for example by cellulases, hemicellulases, pectinases, hydrolases), and very high pressure destructuring (500 to 5000 bars), sonication, in particular to favor the extraction of the substances of interest sought.

However, these treatments often prove completely or partially destructive for the components, in particular biologically active components, contained in the plant cells.

There is therefore a real need to improve the personal extraction, i.e., to obtain substances of interest easily and quickly that are located at the heart of the cells of the plants and with the highest possible output coupled with minimal deterioration of said substances. The invention therefore aims to seek the most complete possible personal extraction, thereby making it possible to increase the content level of the retrieved substances, which are originally contained in a plant cell, relative to the solutions existing in the prior art.

The present invention therefore relates to a method for producing articles impregnated with at least one plant substance from at least one plant, characterized in that it comprises the following steps:

a) Extraction and/or pressing of at least one plant (V1), or at least one part of said plant, producing a liquid plant extract (E1) and a solid fibrous residue (R1), then b) Separation of said plant extract (E1) from said fibrous residue (R1), and c) Destructuring of said fibrous residue (R1), d) Production of a fibrous web or of an article made from the fibrous residue (R1) obtained in step c), and e) impregnation of said fibrous residue (R1) with (i) at least said plant extract (E1), which is optionally concentrated, purified, flavored and/or fragranced, with (ii) at least one water-soluble or liposoluble plant substance isolated from said plant extract (E1), with (iii) at least one composition comprising at least one optionally concentrated, purified, flavored and/or fragranced water-soluble or liposoluble substance of said plant extract (E1), or with (iv) at least one plant extract (E2) or at least one composition comprising at least one optionally concentrated, purified, flavored and/or fragranced water-soluble or liposoluble substance of said plant extract (E2), resulting from an extraction or pressing of a plant (V2) different from said plant (V1).

According to one embodiment of said method, step c) precedes step d), which in turn precedes step e).

Lastly, according to another embodiment of said method, step c) precedes step e), which precedes step d).

The invention also relates to an article of plant origin comprising a compact, homogenous solid structure of plant fibers, said structure being impregnated with at least one plant extract, which is optionally concentrated, purified, flavored, colored and/or fragranced, (ii) at least one water-soluble or liposoluble plant substance isolated from a plant extract, or (iii) at least one composition comprising at least one water-soluble or liposoluble substance of a plant extract that may optionally be concentrated, purified, flavored, colored and/or fragranced.

BRIEF DESCRIPTION OF THE INVENTION

The plant may be chosen from among food plants, medicinal plants, aromatic plants and fragranced plants.

Aromatic plants include rosemary, sage, thyme, mint, oregano, turmeric, basil and cloves.

Food plants include stevia, garlic, tea and coffee.

Medicinal plants include willow, ginseng, ginkgo, red vine, green tea and sagebrush.

The plant may for example be chosen from among plants containing at least one substance chosen from among antioxidants, sweetening agents, perfumes, flavors, carotenoids, xanthophylls, dyes, flavonoids, tannins, polyphenols, peptides, vitamins, proteins, and pharmaceutical active ingredients.

Said active ingredients include salicin from willow bark, gingkolides from *ginkgo biloba* leaves, hyperforin from St. John's wort blossom, artemisinin from the leaves and stems of artemisia annua, curcumin from *curcuma longa* roots, genistein and daidzein from soya seeds, gingsenoides from ginseng roots, anthocyanosides and tannins from red vine leaves and stevioside from stevia rebaudiana leaves.

Advantageously, the plant is chosen from among rosemary, sage, thyme, mint, oregano, turmeric, basil, cloves, stevia, tea and coffee

DETAILED DESCRIPTION

Figure 1:
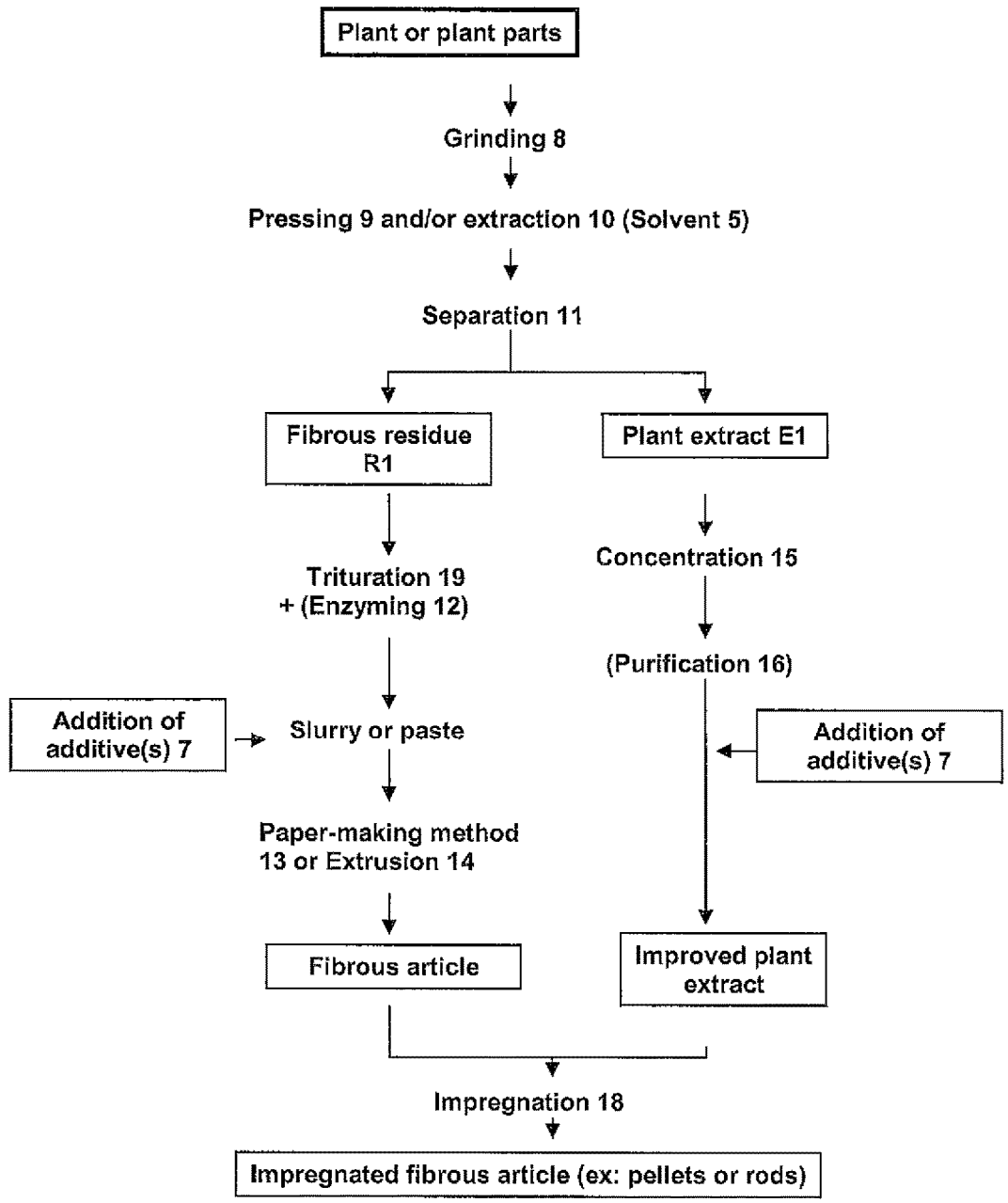
FIG. 1 shows a method according to the invention wherein the fibrous residue article, for example a pellet or a rod, is impregnated by a plant extract after being produced.

The method according to the invention comprises an extraction and/or pressing step followed by a step for separating the insoluble products or fibrous residues (R1) of a plant (V1) or part of a plant from the soluble substances or plant extract (E1).

Before the extraction and/or pressing steps, an optional grinding/chopping step may be carried out. The purpose is to pull apart the plant or plant part, and therefore to break down the walls of the plant cells.

The extraction and/or pressing may be done on at least one plant part, which is fresh, frozen or dried, chosen from among the roots, bark, seeds, stems, leaves, flowers and fruits.

The extraction may be done by pressing and/or extraction of vegetal substances, in particular plants, with at least one solvent at ambient temperature and atmospheric pressure, said solvent being able to be chosen from among water, ethanol, hexane, acetone and hydrofluorocarbons. Other extraction methods may be used involving at least one solvent, for example such as R134a or carbon dioxide and at different temperatures, different pressures and different states (liquid or gas). It is for example possible to use a solvent such as, for example, chosen from among the solvents mentioned above, or, if applicable, carbon dioxide:
   in liquid state (volatile and non-volatile solvents at ambient temperature),
   in subcritical state (water at a temperature above 100° C. and a pressure above 1 bar), or
   in supercritical state ($CO_2$ at a temperature above 31° C. and a pressure above 73 bars).

The solvent/plant weight ratio is generally from 1 to 10.

The separation step can be carried out by separating the resulting liquid phase from the resulting solid phase by filtration, with or without pressure, by centrifugation or by any other methods commonly used in the laboratory.

According to one embodiment, the solid-liquid extraction is done by using a solvent with which the plant or at least part of the plant, optionally cut and/or ground beforehand, is put in contact, then separating the obtained liquid phase from the solid phase consisting of the plant by filtration with or without pressure or by centrifugation during a separation step.

According to another embodiment, the solid-liquid extraction is done by hydrodistilling the plant or at least part of the plant, optionally cut and/or ground, with water as the solvent, then separating the resulting organic and aqueous phases.

These extraction methods may be coupled with or assume the form of an extraction using microwaves, for example such as the vacuum microwave hydrodistillation method (VMHD), the microwave assisted process (MAP), and the microwave-assisted solvent extraction method (MASE), or by using ultrasounds such as sonication.

These extraction methods may be continuous or discontinuous.

The methods and, if applicable, the solvent(s) may be chosen to meet the requirements of the regulations for organic products and environmental protection.

Once the soluble substances are separated from the fibrous residues, the method according to the invention may optionally comprise a step for concentrating the soluble substances or plant extract in a liquor, and/or a step for isolating at least one soluble substance from the extract or said liquor, or even a purification or elimination step with respect to any impurities that may be present so as to obtain a purified extract, a purified liquor or at least one isolated, purified soluble substance, in which at least one additive can also be incorporated. The original raw plant extract is thus converted into an improved plant extract, whether in the form of dry extracts, liquid extract, a liquor or an isolated substance.

Said additive may be chosen from among (i) flavorings, for example such as menthol, licorice, fruit extracts in general, (ii) fragrances, and (iii) dyes, for example such as caramel, beet red, anthocyanins and copper chlorophyllin.

The concentration, isolation and purification steps are done by means of the techniques typically used in the laboratory.

The method according to the invention further comprises a step for destructuring the insoluble products or solid fibrous residues (R1) using a method that may be mechanical, chemical and/or biological, advantageously a mechanical method coupled with a biological method.

The fibrous residue may be treated using a violent agitation mechanical method or a simple mechanical abrasion and splitting method, during a trituration step that may, for example, be assisted by ultrasounds. The fibrous residue may thus be converted into a slurry, i.e., a non-homogenous liquid mixture, advantageously aqueous, containing whole fibers or partially destroyed fibers or in a paste, i.e., a homogenous liquid mixture, advantageously aqueous, the consistency of the mixture depending on the intensity and duration of said destructuring step.

According to one embodiment, the destructuring step may occur through mechanical shearing and friction of the fibrous residue between a rotor and a stator, optionally accompanied by ultrasounds.

The fibrous residue may be biologically treated. The fibrous residue may be (i) sown by yeasts, advantageously by yeasts chosen from the *Saccharomyces* genus or may be (ii) mixed with a sufficient quantity of water to form a liquid paste, then it is sown by enzymes, advantageously enzymes chosen from among enzymes with pectinase, cellulase, amylase activities and mixtures thereof.

The purpose of this biological step is to partially reduce the size of the fibers, in particular cellulose, lignin and pectin. For example, a certain liquefaction of the fibrous residue and elimination of ballast may be obtained by adding at least one enzyme chosen for example from among the enzymes defined above.

It is also possible to add, to the fibrous residue, at least one additive of natural origin, optionally chosen from among (i) binders, for example such as gum Arabic and guar gum, (ii) carbon hydrates of plant origin, optionally chosen from among glucose and invert sugars, (iii) products of animal source, optionally chosen from among chitin deacetylase and marine plant gums, such as alginates, carrageenans and agar-agar, (iv) reinforcing fibers, for example such as cereal straw, bagasse, cotton, pine or eucalyptus fibers, (v) flavorings, for example such as menthol, licorice, fruit extracts in general, (vi) dyes, advantageously a water-soluble natural dye for example chosen from among caramel, beet red, anthocyanins and copper-chlorophyllin, (vii) fragrances and (viii) various fillers.

The method according to the invention then comprises a step for producing a fibrous web or an article made from insoluble products or fibrous residues assuming the form of a slurry or paste as defined above. The production of said fibrous web may be done using a method of the papermaking type, and the shaping of said fibrous article may be done by extrusion, thereby making it possible to obtain a more or less expanded solid article. During the shaping step, the shaped articles may assume the tom, of sheets, rods, pellets, fibers, solid or hollow, or chips.

The method lastly comprises an incorporation step (also called impregnation step) for (i) said soluble substance liquor, optionally purified, or (ii) at least said isolated soluble substance, optionally concentrated, or (iii) at least one liquor of plant origin or (iv) a plant extract, in the fibrous web or directly in the fibrous residues resulting from the separation step, or even the slurry or the paste, obtained at the end of the destructuring step, and/or comprises a step for impregnating the shaped articles.

During the impregnation step e) of the fibrous residue, the latter may also be impregnated with (i) at least one dye, advantageously at least one water-soluble natural dye chosen from among caramel, beet red, anthocyanins and copper-chlorophyllin and/or with (ii) at least one water-soluble food fiber of plant or animal origin chosen from among carrageenans, alginates, pectins, starches and xanthans, caseins and gelatins, advantageously a water-soluble food fiber of plant origin.

After drying, articles of plant origin are then obtained comprising a compact solid structure of plant fibers, said structure being impregnated by at least one plant extract, optionally concentrated, purified, flavored, colored and/or fragranced, (ii) at least one water-soluble or liposoluble plant substance isolated from a plant extract, or (iii) at least one composition comprising at least one water-soluble or Liposoluble substance of a plant extract, optionally concentrated, purified, flavored, colored and/or fragranced. The extract of plant origin may be chosen from among extracts of roots, seeds, stems, leaves, flowers, fruits, or mixtures thereof.

According to one embodiment of the present invention relative to FIG. 1, the method consists of separating the soluble substances or ingredients forming the plant extract (3a) on the one hand, and the insoluble substances, i.e., the fibrous residues (2a) of the plant as raw material on the other hand. To that end, the plant, in dry, fresh or frozen form, may be ground/or cut beforehand during a grinding/cutting step (8).

The pressing (9) or extraction (10) step is then done by using a solvent (5), preferably water, a pure ethyl alcohol or in a hydroalcoholic mixture or any other suitable solvent, pure or in a mixture, whether cold, at ambient temperature or at a temperature higher than the boiling point of the solvent(s) used, optionally with prior maceration of the plant, which may optionally be ground beforehand.

According to one alternative of the method, the extraction (10) is assisted by microwaves and impulsive vacuum (method described in document EP 0,698,076 entitled "Method and plant for solvent-free microwave extraction of natural products," known under the name VMHD). In this case, the obtained plant extract, i.e., the water of constitution of the plant augmented by essential oils, is directly reincorporated into the fibrous residue. Using this rapid and low-temperature extraction method, the absence of deterioration of the essential oils and other floral waters obtained has been observed, Leading, after impregnation, to increased naturalness, in particular olfactory, of the impregnated articles according to the invention.

The separation (11) of the soluble substances forming the plant extract (3a) and the insolubles forming the fibrous residue is traditionally done by filtration through a filtering medium such as a canvas, a grate, or by centrifugation.

According to one alternative of the method, the plant in fresh or thawed form and rich in water (wt % of water greater than 50% relative to the total weight of the plant) can be treated directly by pressing (9) and provide plant extract (3a) on the one hand and the insoluble substances or fibrous residue (2a) on the other hand.

The plant extract (3a) is a solution that can be concentrated during a concentration step (15) by partial evaporation of the solvent under the combined effect of the vacuum and the temperature or by filtration on a selective membrane (reverse osmosis or ultrafiltration method) (15).

If necessary, the plant extract (3a) can be purified during a purification step (16) by passing over a column provided with an absorbent or a resin or purified by selective extraction by a solvent that is not miscible with the plant extract in solution.

At this stage, the excess content of mineral matter in certain plants (silica, potassium, calcium, etc.) can also be reduced by spontaneous or induced decanting and precipitation.

The plant extract (3a) can also be enriched by at least one additive (7) chosen from among (i) flavorings such as menthol, licorice, fruit extract in general, and (iv) dyes. One then obtains an improved plant extract (3b).

The fibrous residue (2a) is treated through a physical violent agitation process or simple mechanical abrasion and splitting, during a trituration step (19) may for example be assisted by ultrasound, and said residue is thus converted into a non-homogenous aqueous sludge containing whole or partially destroyed fibers.

According to one alternative of the method, the fibrous residue is biologically treated during an enzyming step (12) described above.

At the end of the trituration step (19) or the trituration step followed by the enzyming step (12), a paste is obtained defining a homogenous mixture or a slurry defining a non-homogenous mixture due to a coarse and incomplete trituration.

The slurry or paste may be enriched by at least one additive (7) chosen from among (i) reinforcing fibers, for example such as cereal straw, cotton, or eucalyptus fibers, (ii) humectants, for example such as glucose and invert sugars, (iii) flavorings, for example such as menthol, licorice, fruit extract in general, (iv) dyes and (v) miscellaneous fillers.

The slurry or paste of fibrous residue can then be converted using common paper-making techniques according to a paper-making method (13), continuously or discontinuously, into an article (2b), for example a fibrous web also called a paper web or extruded during extrusion step (14).

In particular through a simple method, the paste or slurry is spread on an endless metal strip and dried by air, thereby forming a sheet of paper. However, many other methods for manufacturing paper sheets are known, for example methods using stratification or pressing.

The improved plant extract (3b), which may optionally be concentrated, purified, flavored and/or colored, is introduced into the fibrous residues by spraying or any other impregnation method (18).

According to one alternative of the method, the plant extract, optionally concentrated, purified, flavored and/or colored, is mixed with the paste or the slurry before the paper-making method or the extrusion (14) forming an article (2b), for example a fibrous web.

According to another alternative of the method, the shaping of an article according to the invention, for example a rod or a pellet, is done using an extrusion method. The impregnation by the improved plant extract (3b) is then done simultaneously with or after the shaping of the articles by the extruder (14).

Figure 2:
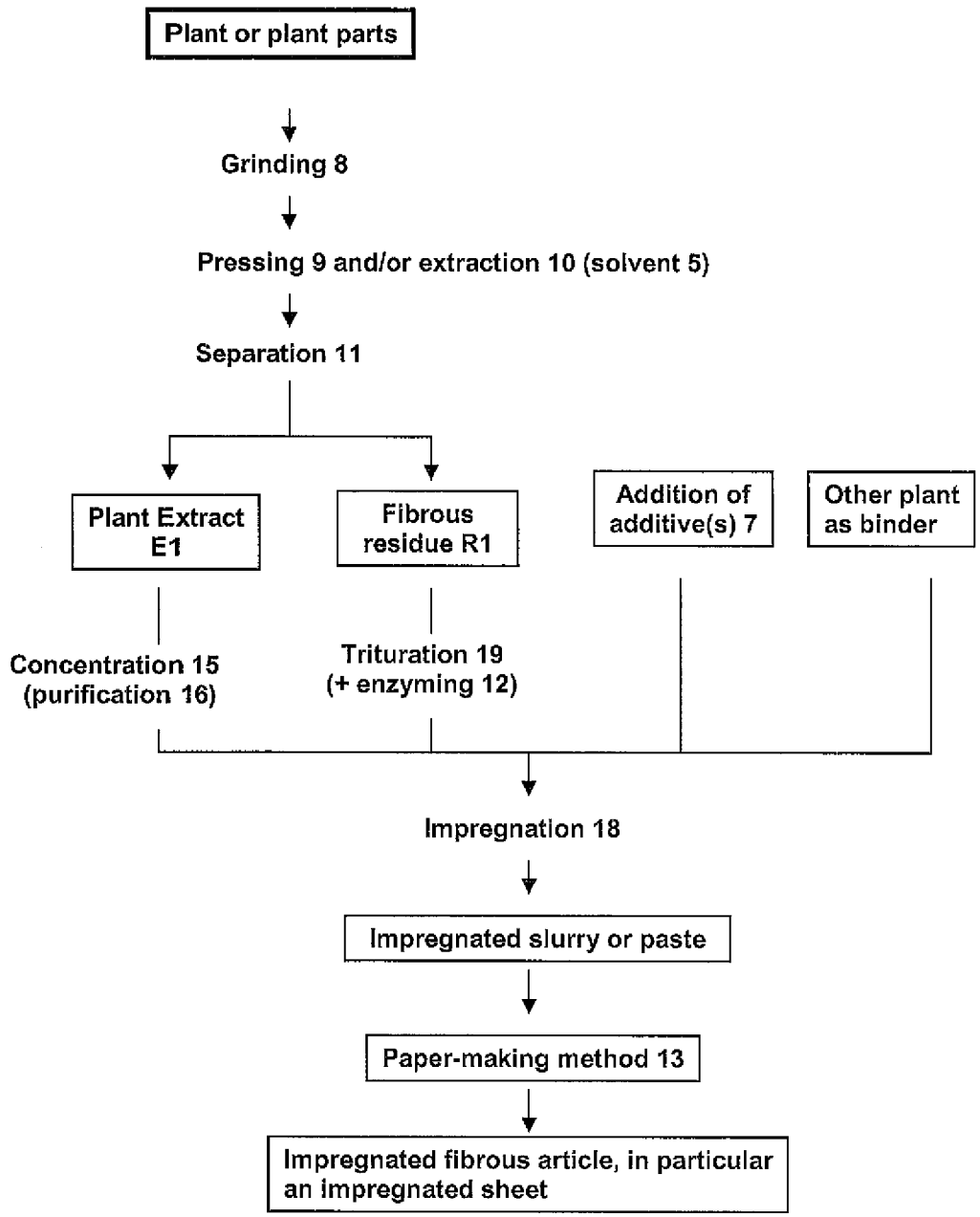
FIG. 2 shows a method according to the invention wherein a slurry or a fibrous paste made from at least one plant is impregnated by at least one plant extract previously isolated from said plant or from another plant, prior to the shaping method.

According to another embodiment of the present invention relative to FIG. 2, the method according to the invention comprises an extraction (10) and/or pressing (9) step followed by a separation step (11) of the insoluble products or fibrous residues (R1) of a plant (V1) or part of a plant from the soluble substances or plant extract (E1).

Before the extraction (10) and/or pressing (9) steps, an optional grinding/cutting step (8) may be carried out. The purpose of this step is to pull apart the plant or plant part and therefore break the walls of the plant cells.

The extraction and/or pressing may be done on at least one plant part, which may be fresh, frozen or dried, chosen from among the roots, bark, seeds, stem, leaves, flowers and fruits.

The extraction (10) can be carried out by pressing (9) and/or vegetal substance extraction (10), in particular from plants, with at least one solvent (5) at ambient temperature and atmospheric pressure, said solvent being able to be chosen from among water, ethanol, hexane, acetone and hydrofluorocarbons. Other extraction methods may be used involving at least one solvent, for example such as R134a or carbon dioxide and at different temperatures, different pressures and in different states (liquid or gas). It is for example possible to use a solvent for example chosen from among the aforementioned solvents or, if applicable, carbon dioxide:
   in liquid state (volatile and non-volatile solvents at ambient temperature),
   in subcritical state (water at a temperature above 100° C. and a pressure above 1 bar), or
   in supercritical state (the $CO_2$ has a temperature above 31° C. and pressure above 73 bars).

The solvent/vegetal substance ratio is generally from 1 to 10.

Said separation step (11) can be carried out by separating the resulting liquid phase from the resulting solid phase by filtration, with or without pressure, by centrifugation, or using any other methods commonly used in the laboratory.

According to one embodiment, the solid-liquid extraction is done by using a solvent with which the plant or at least part of the plant is put in contact, optionally previously cut and/or ground, then by separating the obtained liquid phase from the solid phase made up of the plant by filtration with or without pressure or by centrifugation during a separation step.

According to another embodiment, the solid-liquid extraction is done by hydrodistilling the plant or at least part of the plant, optionally cut and/or ground, with water as solvent, then separating the resulting organic and aqueous phases.

These extraction methods may be coupled with microwave-assisted extraction, for example such as the vacuum microwave hydrodistillation method (VMHD), the microwave assisted process method (MAP), and the microwave-assisted solvent extraction method (MASE), or by using ultrasounds, such as sonication.

These extraction methods may be continuous or discontinuous.

The methods and, if applicable, the solvent(s) may be chosen to meet the requirements of the regulations for organic products and environmental protection.

Once the soluble substances are separated from the fibrous residues, the method according to the invention may optionally comprise a concentration step (15) for the soluble substances or plant extract into a liquor, and/or a step for isolating at least one soluble substance from the extract or from said liquor, or a purification step (16) or elimination step for any impurities that may be present so as to obtain a purified extract, a purified liquor or at least one isolated, purified soluble substance. The concentration, isolation and purification steps are done by means of the techniques typically used in the laboratory.

The method according to the invention also comprises a destructuring step (19) for the insoluble products or solid fibrous residues (R1) using a method that may be mechanical, chemical and/or biological, advantageously a mechanical method coupled with a biological method.

The fibrous residue may be processed using a mechanical violent agitation method or a simple mechanical abrasion and splitting method, during a trituration step that may be assisted, for example, by ultrasound.

The fibrous residue may thus be converted into a slurry, i.e., a non-homogenous liquid mixture, advantageously aqueous, containing whole or partially destroyed fibers or in a paste, i.e., a homogenous liquid mixture, advantageously aqueous, the consistency of the mixture depending on the intensity and duration of said destructuring step.

According to one embodiment, the destructuring step may occur by mechanical shearing and friction of the fibrous residue between a rotor and a stator, optionally accompanied by ultrasound.

The fibrous residue may be treated biologically. The fibrous residue may be (i) sown by yeasts, advantageously by yeasts chosen from the Saccharomyces genus or can be (ii) mixed with a sufficient quantity of water to form a liquid paste, then is sown by enzymes, advantageously enzymes chosen from among enzymes with a peptidase, cellulase, amylase activity and mixtures thereof. This is then called an enzyming step (12).

The purpose of this biological step is to partially reduce the size of the fibers, in particular cellulose, lignin and pectin.

At least one additive (7) can be added to the plant extract (E1), which may optionally be concentrated or even purified. Said additive is chosen from among (i) flavorings, for example such as menthol, licorice, fruit extracts in general, (ii) fragrances and (iii) dyes, for example such as caramel, beet red, anthocyanins, and copper-chlorophyllin and/or at least one additive (7) of natural origin may be added to the slurry or the fibrous residue paste, said additive then optionally being chosen from among (i) binders such as, for example, gum Arabic and guar gum, (ii) carbon hydrates of plant origin, optionally chosen from among glucose and invert sugars, (iii) animal source products, optionally chosen from among chitin deacetylase and marine plant gums, such as alginates, carrageenans and agar-agar, (iv) reinforcing fibers, for example such as cereal straw, bagasse, cotton, pine or eucalyptus fibers, (v) flavorings, for example such as menthol, licorice, fruit extracts in general, (vi) dyes, advantageously a water-soluble natural dye for example chosen from among caramel, beet red, anthocyanins and copper-chlorophyllin, (vii) fragrances and (viii) various fillers.

The method then comprises an incorporation step, also called impregnation step (18), for incorporating (i) said liquor of optionally purified soluble substances or (ii) at least said isolated soluble substance, optionally concentrated or (iii) at least one liquor of plant origin or (iv) a plant extract, in a slurry or paste, obtained at the end of the destructuring step.

The method according to the invention next comprises a step for producing a fibrous web or paper-making method (13) leading to the formation of an impregnated fibrous article, in particular an impregnated sheet.

Figure 3:
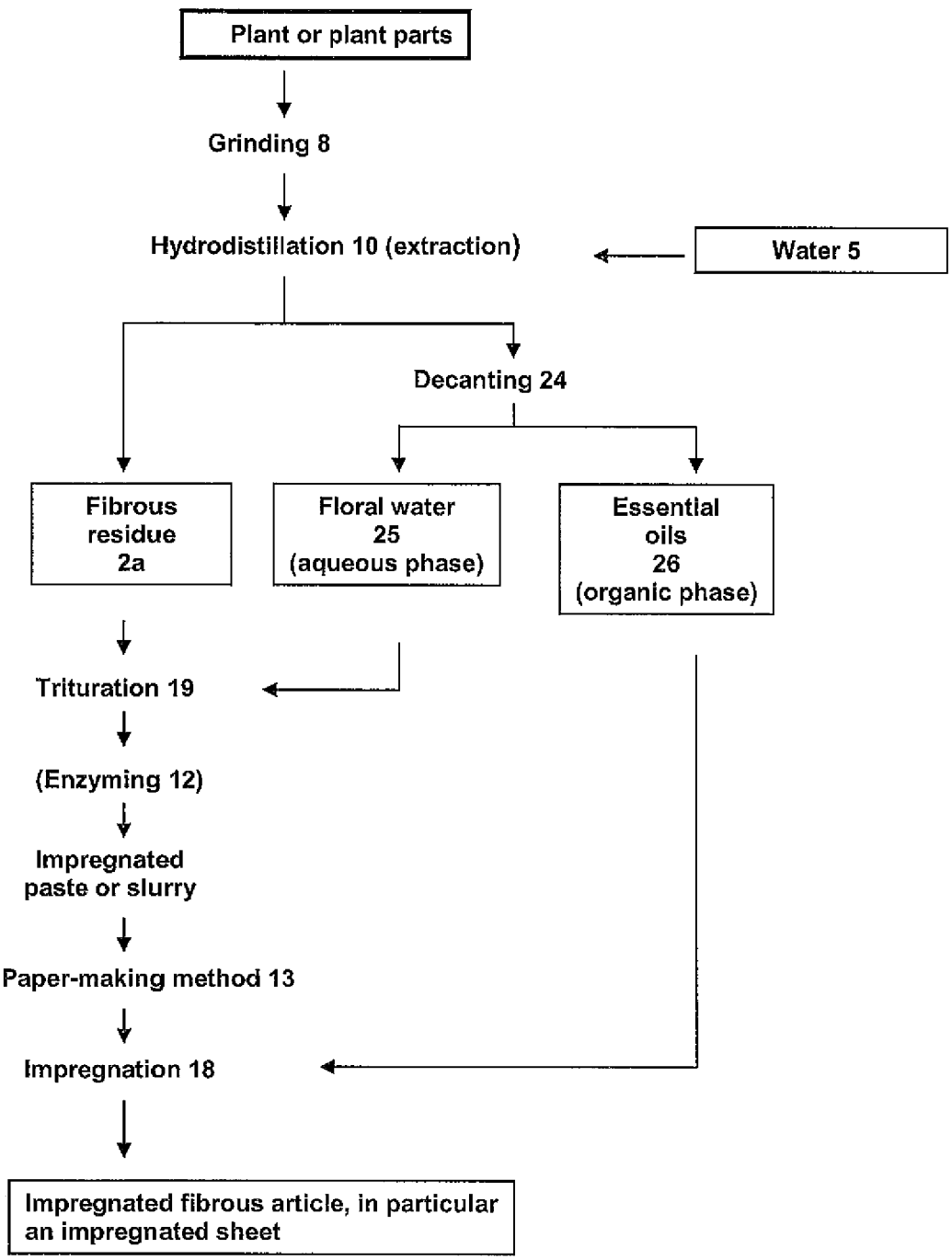
FIG. 3 shows a method according to the invention wherein the essential oils of a starting plant are extracted using steam, then after separation of the aqueous phase and the organic phase, the extraction water can be used to impregnate a slurry or a paste made from the fibrous residue while the essential oils may optionally be used to impregnate the articles made by said slurry or paste. Said articles may assume the form of reconstituted plant parts.

According to still another embodiment of the present invention relative to FIG. 3, the method according to the invention comprises a step for extracting soluble substances or plant extract (El) from a plant (V1) by hydrodistillation with water as the solvent followed by a decanting step (24) for the aqueous and organic phases obtained at the end of the hydrodistillation, the organic phase containing the essential oils (26) of said plant (E1) and the aqueous phase containing the floral water (25) of said plant (V1).

One thus obtains the separation of the insoluble products or fibrous residues (R1) of the plant (V1) or part of a plant from the soluble substances, i.e., the floral water (25) and the essential oils (26).

Before the hydrodistillation step (10), an optional grinding/cutting step (8) may be carried out. The purpose of this step is to pull apart the plant or plant part and therefore break the walls of the plant cells.

The hydrodistillation may be done on at least a plant part, fresh, frozen or dried, chosen from among the roots, bark, seeds, stems, leaves, flowers and fruits.

The method according to the invention also comprises a destructuring step for the insoluble products or solid fibrous residues (R1) through a method that may be mechanical, chemical and/or biological, advantageously a mechanical method coupled to a biological method.

The fibrous residue may be treated using a violent agitation mechanical method or a simple mechanical abrasion and splitting method, during a trituration step (19) that may for example be assisted by ultrasound. The fibrous residue may thus be converted into a slurry, i.e., a non-homogenous liquid mixture, advantageously aqueous, containing whole or partially destroyed fibers or a paste, i.e., a homogenous liquid mixture, advantageously aqueous, the consistency of the mixture depending on the intensity and duration of said destructuring step.

According to one embodiment, the destructuring step may occur through mechanical shearing and friction of the fibrous residue between a rotor and a stator, optionally accompanied by ultrasound.

The fibrous residue may be biologically treated. The fibrous residue may be (i) sown by yeasts, advantageously yeasts chosen in the *Saccharomyces* genus, or may be (ii) mixed with a sufficient quantity of water to form a liquid paste, then sown by enzymes during an enzyming step (12), advantageously enzymes chosen from among enzymes with pectinase, cellulase, amylase activities and mixtures thereof.

The purpose of this biological step is to partially reduce the size of the fibers, in particular cellulose, lignin and pectin fibers. For example, a certain liquefaction of the fibrous residue and elimination of ballast may be obtained by adding at least one enzyme, for example chosen from among the enzymes defined above.

At the end of the trituration step (19) or the trituration step followed by the enzyming step (12), a paste is obtained defining a homogenous mixture or a slurry defining a non-homogenous mixture due to a coarse and incomplete trituration.

The slurry or the paste is then impregnated during an impregnation step (18) by the floral water (25). It may also optionally be enriched by at least one additive (7) chosen from among (i) reinforcing fibers, for example such as cereal straw, cotton or eucalyptus fibers, (ii) humectants, for example glucose and invert sugars, (iii) flavorings, for example such as menthol, licorice, fruit extracts in general, (iv) dyes and (v) various fillers.

Next, the slurry or the paste of fibrous residue may then be converted using common paper-making techniques according to a paper-making method (13), continuously or discontinuously, into an article (2b), for example a fibrous web also called a paper-making web.

In particular through a simple method, the paste or slurry is spread on an endless metal strip and dried by air, thereby forming a sheet of paper. However, many other methods for manufacturing paper sheets are known, for example methods using stratification or pressing.

The method lastly comprises an impregnation step (18) of the fibrous web obtained at the end of the paper-making method (13) by the essential oils (26).

During the impregnation step (18) of the fibrous residue of the fibrous web, the latter may also be impregnated with (i) at least one dye, advantageously a water-soluble natural dye chosen from among caramel, beet red, anthocyanins and copper-chlorophyllin and/or with (ii) at least one water-soluble food fiber of plant or animal origin chosen from among carrageenans, alginates, pectins, starches and xanthans, caseins and gelatins, advantageously a water-soluble food fiber of plant origin.

At the end of this method, an impregnated fibrous article is obtained, in particular an impregnated sheet.

Through an alternative of the wet methods with extraction-reincorporation of substances of interest, the invention also applies to reconstituted plant materials obtained through a dry method by placing, in direct contact, pure plant materials or plant materials mixed in a practically dry form with or without a binding agent and/or other added substances, then mixed and subjected to a high cutting and degradation agitation level in the presence of a relatively low water content (moisture level less than approximately 30%). The material thus prepared is then subsequently treated in a sheet-making (pressing or rolling) and cutting device using dry techniques so as to obtain reconstituted plant materials.

The articles according to the invention, which may be obtained according to one of the embodiments of the method presented above, may for example be decorative articles such as articles in the form of reconstituted plant sheets, flowers, etc., or may be articles such as sheets of paper with different thicknesses, filaments, pellets, chips or tubes. These articles may optionally be ground, making it possible to generate powder particles of de-structured and impregnated plants.

Advantageously, the powder is designed to be incorporated into pharmaceutical compositions, cosmetic compositions, food compositions, and/or dietary compositions.

The method may be used with plants in a mixture, making it possible to seek out an original synergy as already observed in Chinese medicine and ayurverdic medicine.

The articles that may be obtained using the method according to the invention have the advantage of:
being able to be used directly, for example to produce herbal teas or infusions that may have medicinal, cosmetic, dietary and/or nutraceutical properties,
or then finely ground, so as to be able to be incorporated
(i) into galenic forms, for example such as capsules, or
(ii) in many compositions for topical or oral applications (for example, in syrups, chewing gums, gels, lotions, creams, emulsions), said compositions being able to be intended to be used for food, dietary, medicinal, nutraceutical or cosmetic purposes.

The articles according to the invention also have the advantage relative to the products traditionally used of being of high quality, since the soluble substances that may be partially destroyed or completely modified by the trituration and paper-making manufacturing methods are temporarily separated from the fibrous fraction undergoing the treatments. In particular through this operation, the sensory properties of the plants are remarkably preserved.

They may be dosable as active ingredients during the incorporation of the liquor or plant extract in the paper fibrous web and provided without bothersome substances (for example pesticides, toxic substances, and other allergenics) that may be eliminated during the method.

The plant raw materials used to produce the articles according to the invention may be made up of whole plants or plant parts, in particular stems, bark, seeds and plant waste (dust, ribs, and debris). The raw material may be dry, moist, fresh, fermented or roasted.

The articles according to the invention have a homogenous structure (no ribs) and may have a planar and constant surface with a good visual output.

The active ingredients are easily extractable from the articles according to the invention by the human body in the event of ingestion or contact with the skin or hair, since the elements that may oppose easy extraction (fibers, membranes, tannins, etc.) have been eliminated or modified. The same result is observed during the use of the articles according to the invention in herbal teas. Consequently, the products according to the invention, when reduced into powder, fundamentally differ from the powders available on the market produced solely by grinding plants or plant parts (cryogrinding, micronization, etc.) without destructuring treatment of the ballast surrounding the active substances of interest.

The controlled water content of the finished product of the method according to the invention guarantees a better bacteriological quality than the plants, herbal teas and powders traditionally used as is, without physical or chemical decontamination.

The method according to the invention makes it possible to produce sheets of paper with a variable thickness that may be cut by cutting punches of various shapes and may also assume a three-dimensional form through molding or extrusion, optionally making it possible to form articles with decorative shapes, having a precisely defined density and permeability unsuitable for their final use.

The method according to the invention may be done without adding any substance other than plants or plant parts and water (organic and 100% natural method) but, nevertheless, if justified, the method allows the homogenous addition of substances in the finished product, for example flavorings, dyes, other active ingredients (antioxidants, vitamins, etc.), binders, and if necessary, reinforcing fibers (cereal straws, bagasse, linen or cotton fibers, etc.).

Other advantages may also appear to one skilled in the art upon reading the examples below, illustrated by the appended figures, provided as an illustrative example.

EXAMPLES

Example 1

(see FIG. 2)

The method consists of coarsely grinding, by shearing, blossoms (flowers, stems and leaves) of fresh mint (*Mentha x piperita*) and extracting the active ingredients from the water (ground plant/water ratio 1/5, at a temperature kept at 60-70° C. for 15 min. with agitation), then separating the soluble extract from the insoluble parts by mechanical pressing. The operation is repeated 2 times.

The first extract is half concentrated by evaporation and the fibrous fraction is triturated in the presence of water (rotor/stator dispersion/homogenization by an Ultra-Turrax IKA) until a paste is formed.

A liquid solution of 10% menthol is prepared and kept at 40° C.

1% of the products and all of the concentrate are then mixed with the destructured mint insolubles alone or mixed with finely pulverized tea leaves (*Camelia sinensis*) and/or leaves and stems of *Stevia rebaudiana* and forming, by pouring or extrusion of said mixture, a reconstituted sheet. The sheet can then be dried and cut, The cut sheet is used as such in a traditional infusion or in infusion packets after grinding. The menthol content of the product is very high. In one alternative of the method, essential mint oils are substituted for the menthol solution.

Example 2

(see FIG. 3)

The method consists of hydrogen distilling, at atmospheric pressure, 100 g of dried rosemary blossoms (*Rosmarinus officinalis*) (mixture of tough leaves, fibrous stems, twigs and flowers) by 2 of steam. Then, after condensation of the steam and cooling, the method consists of separating the upper phase, i.e., approximately 0.5 mL of essential oil, from the lower phase (white water for approximately 1.5 l).

The essential oil is a very fluid, colorless to pale yellow fluid. It is known for containing borneol, cineole, camphene, pinene and chlorogenic acid. The rosmarinic acid, which is a powerful antioxidant, is divided between the aqueous phase, the essential oil and the solid residue. The floral water or white water is concentrated 5 times under vacuum at a temperature not exceeding 60° C., then is added to the insoluble residue of the distillation of the rosemary.

The whole is agitated violently (Ultra turax IKA) until it forms a paste, which is sown by an enzyme cocktail (Peclyve CP and EP by Lyven in a 50/50 mixture) at 1 wt % for 3 hours at 45° C. The slurry is then poured into a mold and pressed. After drying by hot air, the film formed is impregnated by spraying with the essential oil in an alcohol solution.

The invention claimed is:

1. A method for producing fibrous web and/or article impregnated with a plant extract comprising:
   a) extracting or pressing a plant or at least one part of the plant, thereby producing a liquid plant extract and a solid fibrous residue, wherein the plant is selected from the group consisting of rosemary, sage, thyme, mint, oregano, turmeric, basil, cloves, stevia, garlic, coffee, willow, ginseng, ginkgo, red vine, St. John's wort, artemisia, Curcuma, and soya,
   b) separating the liquid plant extract from the solid fibrous residue,
   c) destructuring the solid fibrous residue,
   d) producing a fibrous web or an article from the destructured solid fibrous residue obtained in step c), and
   e) impregnating the destructured solid fibrous residue or the article obtained in step d) with the separated liquid plant extract obtained in step b).

2. The method according to claim 1, wherein the extraction or pressing step a) is done on at least one plant part, fresh, frozen or dry, chosen from among the roots, bark, seeds, stem, leaves, flowers and fruits.

3. The method according to claim 1, wherein the extraction is an extraction chosen from among supercritical $CO_2$ extraction, solid-liquid extraction using a solvent and subcritical extraction, optionally coupled with or assuming the form of an extraction assisted by ultrasound or microwave.

4. The method according to claim 3, wherein the solvent is chosen from among water, ethanol and hexane, or wherein the solvent to plant weight ratio is from 1 to 10.

5. The method according to claim 3, wherein the solid-liquid extraction is done by using a solvent that is brought into contact with the plant or at least part of the plant, the plant being optionally cut or ground beforehand, then separating the obtained liquid phase from the solid phase by centrifugation.

6. The method according to claim 3, wherein the solid-liquid extraction is done by hydrodistilling the plant or part of the plant, the plant being optionally cut or ground beforehand, with water as the solvent, then separating the resulting organic and aqueous phases.

7. The method according to claim 1, wherein the destructuring step is done using a mechanical, chemical or biological method, or by using a combinations thereof.

8. The method according to claim 1, wherein the destructuring step occurs through mechanical shearing and friction of the solid fibrous residue between a rotor and a stator, optionally accompanied by ultrasounds.

9. The method according to claim 1, further comprising adding an additional fibrous material to the solid fibrous residue, wherein the additional fibrous material is selected from the group consisting of cereal straw, bagasse, cotton, pine and eucalyptus fibers.

10. The method according to claim 1, wherein the solid fibrous residue is biologically treated by being (i) sown with yeasts or (ii) sown with enzymes.

11. The method according to claim 1, wherein the step for producing an article is done by extrusion.

12. The method according to claim 1 wherein the article is in the form of sheets, rods, pellets, solid or hollow fibers, or chips.

13. The method according to claim 1, wherein during the impregnation of the destructured solid fibrous residue, the fibrous web, or the article, the destructured solid fibrous residue, the fibrous web, or the article is also impregnated with (i) at least one dye or with (ii) at least one water-soluble food fiber of plant or animal origin.

14. The method according to claim 10, wherein the yeast is of the Saccharomyces genus.

15. The method according to claim 10, wherein the enzymes are selected from the group consisting of enzymes with pectinase, cellulase, amylase activities and mixtures thereof.

16. The method according to claim 13, wherein the dye comprises at least one water-soluble natural dye selected from the group consisting of caramel, beet red, anthocyanins, and copper-chlorophyllin.

17. The method according to claim 13, wherein the water-soluble food fiber of plant or animal origin is selected from the group consisting of carrageenans, alginates, pectins, starches, xanthans, caseins, and gelatins.

18. The method of claim 1, further comprising impregnating the destructured solid fibrous residue or the article with an additional plant extract.

* * * * *